United States Patent
Hoey et al.

(10) Patent No.: US 8,090,436 B2
(45) Date of Patent: *Jan. 3, 2012

(54) TISSUE DISCRIMINATION AND APPLICATIONS IN MEDICAL PROCEDURES

(75) Inventors: Michael Hoey, Shoreview, MN (US); Corbett Stone, San Diego, CA (US); Kevin Foley, Germantown, TN (US)

(73) Assignee: NuVasive, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/609,004

(22) Filed: Oct. 29, 2009

(65) Prior Publication Data

US 2010/0049081 A1      Feb. 25, 2010

Related U.S. Application Data

(60) Continuation of application No. 11/439,780, filed on May 23, 2006, now abandoned, which is a division of application No. 10/812,038, filed on Mar. 29, 2004, now Pat. No. 7,050,848, which is a division of application No. 09/860,648, filed on May 18, 2001, now Pat. No. 6,760,616.

(60) Provisional application No. 60/205,634, filed on May 18, 2000, provisional application No. 60/243,465, filed on Oct. 25, 2000.

(51) Int. Cl.
*A61B 5/053* (2006.01)
*A61B 17/86* (2006.01)

(52) U.S. Cl. .................. 600/547; 600/554; 606/301

(58) Field of Classification Search ............. 600/547, 600/554; 606/301
See application file for complete search history.

(56) References Cited

U.S. PATENT DOCUMENTS

| | | | |
|---|---|---|---|
| 208,227 A | 9/1878 | Dorr |
| 1,548,184 A | 8/1925 | Cameron |
| 2,704,064 A | 3/1955 | Fizzell et al. |
| 2,736,002 A | 2/1956 | Oriel |
| 2,808,826 A | 10/1957 | Reiner et al. |
| 3,364,929 A | 1/1968 | Ide et al. |

(Continued)

FOREIGN PATENT DOCUMENTS

DE        44 45 593        6/1996

(Continued)

OTHER PUBLICATIONS

"Brackman II EMG System," *Medical Electronics*, 1999, 4 pages.

(Continued)

*Primary Examiner* — Max Hindenburg
*Assistant Examiner* — Emily Lloyd
(74) *Attorney, Agent, or Firm* — Jonathan Spangler; Rory Schermerhorn (57) ABSTRACT

A system and method for discriminating tissue types, controlling the level of therapy to tissue, and determining the health of a known tissue by measuring the characteristics of an electrical signal applied to a conductive element located within or by the tissue. Additionally, the system and method may be used for determining whether the conductive tip of a pedicle probe or pedicle screw is located in one of cortical bone, cancellous bone, and cortical bone near a boundary with soft tissue, whether the conductive tip of a cannula is located adjacent to one of nerve tissue and annulus tissue, and whether the conductive tip of a cathode is located adjacent to one of nerve tissue and prostate gland tissue.

23 Claims, 3 Drawing Sheets

U.S. PATENT DOCUMENTS

| | | |
|---|---|---|
| 3,664,329 A | 5/1972 | Naylor |
| 3,682,162 A | 8/1972 | Colyer |
| 3,785,368 A | 1/1974 | McCarthy et al. |
| 3,830,226 A | 8/1974 | Staub et al. |
| 3,851,641 A | 12/1974 | Toole et al. |
| 3,957,036 A | 5/1976 | Normann |
| 4,099,519 A | 7/1978 | Warren |
| 4,164,214 A | 8/1979 | Stark et al. |
| 4,207,897 A | 6/1980 | Lloyd et al. |
| 4,224,949 A | 9/1980 | Scott et al. |
| 4,235,242 A | 11/1980 | Howson et al. |
| 4,252,130 A | 2/1981 | Le Pivert |
| 4,285,347 A | 8/1981 | Hess |
| 4,291,705 A | 9/1981 | Severinghaus et al. |
| 4,461,300 A | 7/1984 | Christensen |
| 4,515,168 A | 5/1985 | Chester et al. |
| 4,519,403 A | 5/1985 | Dickhudt |
| 4,545,374 A | 10/1985 | Jacobson |
| 4,561,445 A | 12/1985 | Berke et al. |
| 4,562,832 A | 1/1986 | Wilder et al. |
| 4,573,448 A | 3/1986 | Kambin |
| 4,592,369 A | 6/1986 | Davis et al. |
| 4,595,018 A | 6/1986 | Rantala |
| 4,633,889 A | 1/1987 | Talalla |
| 4,658,835 A | 4/1987 | Pohndorf |
| 4,744,371 A | 5/1988 | Harris |
| 4,759,377 A | 7/1988 | Dykstra |
| 4,807,642 A | 2/1989 | Brown |
| 4,892,105 A | 1/1990 | Prass et al. |
| 4,926,865 A | 5/1990 | Oman |
| 4,962,766 A | 10/1990 | Herzon |
| 4,964,411 A | 10/1990 | Johnson et al. |
| 5,007,902 A | 4/1991 | Witt |
| 5,059,602 A | 10/1991 | Effland et al. |
| 5,081,990 A | 1/1992 | Deletis |
| 5,092,344 A | 3/1992 | Lee |
| 5,127,403 A | 7/1992 | Brownlee |
| 5,161,533 A | 11/1992 | Prass et al. |
| 5,196,015 A | 3/1993 | Neubardt |
| RE34,390 E | 9/1993 | Culver |
| 5,255,691 A | 10/1993 | Otten |
| 5,282,468 A | 2/1994 | Klepinski |
| 5,284,153 A | 2/1994 | Raymond et al. |
| 5,284,154 A | 2/1994 | Raymond et al. |
| 5,299,563 A | 4/1994 | Seton |
| 5,312,417 A | 5/1994 | Wilk |
| 5,313,956 A | 5/1994 | Knutsson et al. |
| 5,327,902 A | 7/1994 | Lemmen |
| 5,333,618 A | 8/1994 | Lekhtman et al. |
| 5,375,067 A | 12/1994 | Berchin |
| 5,383,876 A | 1/1995 | Nardella |
| 5,450,845 A | 9/1995 | Axelgaard |
| 5,474,558 A | 12/1995 | Neubardt |
| 5,480,440 A | 1/1996 | Kambin |
| 5,482,038 A | 1/1996 | Ruff |
| 5,484,437 A | 1/1996 | Michelson |
| 5,540,235 A | 7/1996 | Wilson |
| 5,549,656 A | 8/1996 | Reiss |
| 5,560,372 A | 10/1996 | Cory |
| 5,566,678 A | 10/1996 | Cadwell |
| 5,571,149 A | 11/1996 | Liss et al. |
| 5,579,781 A | 12/1996 | Cooke |
| 5,593,429 A | 1/1997 | Ruff |
| 5,599,279 A | 2/1997 | Slotman |
| 5,630,813 A | 5/1997 | Kieturakis |
| 5,671,752 A | 9/1997 | Sinderby |
| 5,707,359 A | 1/1998 | Bufalini |
| 5,711,307 A | 1/1998 | Smits |
| 5,728,046 A | 3/1998 | Mayer |
| 5,741,253 A | 4/1998 | Michelson |
| 5,759,159 A | 6/1998 | Masreliez |
| 5,772,661 A | 6/1998 | Michelson |
| 5,775,331 A | 7/1998 | Raymond et al. |
| 5,779,642 A | 7/1998 | Nightengale |
| 5,785,658 A | 7/1998 | Benaron |
| 5,797,854 A | 8/1998 | Hedgecock |
| 5,806,522 A | 9/1998 | Katims |
| 5,807,272 A | 9/1998 | Kun et al. |
| 5,814,073 A | 9/1998 | Bonutti |
| 5,830,151 A | 11/1998 | Hadzic |
| 5,851,191 A | 12/1998 | Gozani |
| 5,853,373 A | 12/1998 | Griffith et al. |
| 5,860,973 A | 1/1999 | Michelson |
| 5,862,314 A | 1/1999 | Jeddeloh |
| 5,872,314 A | 2/1999 | Clinton |
| 5,885,219 A | 3/1999 | Nightengale |
| 5,888,196 A | 3/1999 | Bonutti |
| 5,902,231 A | 5/1999 | Foley et al. |
| 5,928,139 A | 7/1999 | Koros |
| 5,928,158 A | 7/1999 | Aristides |
| 5,928,159 A | 7/1999 | Eggers et al. |
| 5,947,964 A | 9/1999 | Eggers et al. |
| 5,976,094 A | 11/1999 | Gozani et al. |
| 6,004,262 A | 12/1999 | Putz et al. |
| 6,026,323 A | 2/2000 | Skladnev et al. |
| 6,027,456 A | 2/2000 | Feler et al. |
| 6,038,477 A | 3/2000 | Kayyali |
| 6,050,992 A | 4/2000 | Nichols |
| 6,074,343 A | 6/2000 | Nathanson et al. |
| 6,104,957 A | 8/2000 | Alo et al. |
| 6,104,960 A | 8/2000 | Duysens et al. |
| 6,119,068 A | 9/2000 | Kannonji |
| 6,120,503 A | 9/2000 | Michelson |
| 6,128,576 A | 10/2000 | Nishimoto et al. |
| 6,132,386 A | 10/2000 | Gozani et al. |
| 6,132,387 A | 10/2000 | Gozani et al. |
| 6,135,965 A | 10/2000 | Tumer et al. |
| 6,139,493 A | 10/2000 | Koros et al. |
| 6,146,335 A | 11/2000 | Gozani |
| 6,161,047 A | 12/2000 | King et al. |
| 6,181,961 B1 | 1/2001 | Prass et al. |
| 6,206,826 B1 | 3/2001 | Mathews et al. |
| 6,224,549 B1 | 5/2001 | Drongelen |
| 6,259,945 B1 | 7/2001 | Epstein et al. |
| 6,266,558 B1 | 7/2001 | Gozani et al. |
| 6,292,701 B1 | 9/2001 | Prass et al. |
| 6,306,100 B1 | 10/2001 | Prass |
| 6,312,392 B1 | 11/2001 | Herzon |
| 6,325,764 B1 | 12/2001 | Griffith et al. |
| 6,334,068 B1 | 12/2001 | Hacker |
| 6,337,994 B1 | 1/2002 | Stoianovici et al. |
| 6,425,859 B1 | 7/2002 | Foley et al. |
| 6,425,901 B1 | 7/2002 | Zhu et al. |
| 6,466,817 B1 | 10/2002 | Kaula et al. |
| 6,500,128 B2 | 12/2002 | Marino |
| 6,535,759 B1 | 3/2003 | Epstein et al. |
| 6,564,078 B1 | 5/2003 | Marino et al. |
| 6,719,692 B2 | 4/2004 | Kleffner |
| 6,760,616 B2 | 7/2004 | Hoey et al. |
| 6,796,985 B2 | 9/2004 | Bolger et al. |
| 6,819,956 B2 | 11/2004 | DiLorenzo |
| 6,902,569 B2 | 6/2005 | Parmer et al. |
| 6,929,606 B2 | 8/2005 | Ritland |
| 7,050,848 B2 * | 5/2006 | Hoey et al. ............ 600/554 |
| 7,079,883 B2 | 7/2006 | Marino et al. |
| 7,089,059 B1 | 8/2006 | Pless |
| 7,177,677 B2 | 2/2007 | Kaula et al. |
| 2001/0039949 A1 | 11/2001 | Loubser |
| 2002/0007129 A1 | 1/2002 | Marino |
| 2002/0072686 A1 | 6/2002 | Hoey et al. |
| 2002/0161415 A1 | 10/2002 | Cohen et al. |
| 2006/0224078 A1 | 10/2006 | Hoey et al. |

FOREIGN PATENT DOCUMENTS

| | | |
|---|---|---|
| DE | 299 08 259 | 7/1999 |
| EP | 0 972 538 | 1/2000 |
| FR | 2 795 624 | 1/2001 |
| WO | 95/32673 | 12/1995 |
| WO | 97/11638 | 4/1997 |
| WO | 00/19894 | 4/2000 |
| WO | 00/38574 | 7/2000 |
| WO | 00/66217 | 11/2000 |
| WO | 00/68645 | 11/2000 |
| WO | 01/37728 | 5/2001 |

OTHER PUBLICATIONS

"Electromyography System," *Internal Search Report*, International Application No. PCT/US/00/32329, Apr. 27, 2001, 9 pages.

"Neurovision SE Nerve Locator/Monitor," *RLN Systems, Inc. Operators Manual*, 1999, 22 pages.

The Brackman II EMG Monitoring System, *Medical Electronics Co. Operator's Manual Version 1.1*, 1995, 50 pages.

"The Nicollet Viking IV," *Nicolet Biomedical Products*, 1999, 6 pages.

Calancie et al., "Stimulus-Evoked EMG Monitoring During Transpedicular Lumbosacral Spine Instrumentation," *Spine*, 1994, 19(24): 2780-2786.

Clements et al., "Evoked and Spontaneous Electromyography to Evaluate Lumbosacral Pedical Screw Placement," *Spine*, 1996, 21(5): 600-604.

Darden et al., "A comparison of impedance and electromyogram measurements in detecting the presence of pedicle wall breakthrough," *Spine*, Charlotte Spine Center, North Carolina, Jan. 15, 1998, 23(2): 256-262.

Ebraheim et al., "Anatomic relations between the lumbar pedical and the adjacent neural structures," *Spine*, Department of Orthopaedic Surgery, Medical College of Ohio, Oct. 15, 1997, 22(20): 2338-2341.

Ford et al., "Electrical characteristics of peripheral nerve stimulators implications for nerve localization," *Regional Anesthesia*, 1984, 9: 73-77.

Glassman et al., A prospective analysis of intraoperative electromyographic monitoring of pedicle screw placement with computed tomographic scan confirmation, *Spine*, 1995, 20(12): 1375-1379.

Greenblatt et al., "Needle nerve stimulator-locator: nerve blocks with a new instrument for locating nerves," *Anesthesia & Analgesia*, 1962, 41(5): 599-602.

Holland et al., "Higher electrical stimulus intensities are required to activate chronically compressed nerve roots. Implications for intraoperative electromyographic pedicle screw testing," *Spine*, Department of Neurology, Johns Hopkins University School of Medicine, Jan. 15, 1998, 23(2): 224-227.

Holland et al., "Intraoperative electromyography during thoracolumbar spinal surgery," *Spine*, 1988, 23(17): 1915-1922.

Journee et al., "System for intra-operative monitoring of the cortical integrity of the pedicle during screw placement in low-back surgery: Design and clinical results," *Sensory and neuromuscular diagnostic instrumentation and data analysis*, 18th Annual International Conference on Engineering in medicine and Biology Society, Oct. 1996, 1(31): 144-145.

Lenke et al., "Triggered electromyographic threshold for accuracy of pedicle screw placement," *Spine*, 1995, 20(14): 1585-1591.

Maguire et al., "Evaluation of intrapedicular screw position using intraoperative evoked electromyography," *Spine*, 1995, 20(9): 1068-1074.

Martin et al., "Initiation of erection and semen release by rectal probe electrostimulation (RPE)," *The Williams & Wilkins Co.*, 1983, 637-642.

Minahan et al., The effect of neuromuscular blockade on pedicle screw stimulation thresholds, *Spine*, Department of Neurology, Johns Hopkins University, School of Medicine, Oct. 1, 2000, 25(19): 2526-2530.

Myers et al., "Measurement of vertebral cortical integrity during pedicle exploration for intrapedicular fixation," *Spine*, 1995, 20(2): 144-148.

Pither et al., "The use of peripheral nerve stimulators for regional anesthesia: Review of experimental characteristics, technique, and clinical applications," *Regional Anesthesia*, 1985, 10:49-58.

Raj et al., "Infraclavicular brachial plexus block—A new approach," *Anesthesia* and *Analgesia*, 1973, 52(6): 897-904.

Raj et al., "The use of peripheral nerve stimulators for regional anesthesia," *Clinical Issues in Regional Anesthesia*, 1985, 1(4): 1-6.

Raj et al., "Use of the nerve stimulator of peripheral blocks," *Regional Anesthesia*, Apr.-Jun. 1980, pp. 14-21.

Raymond et al., "The NerveSeeker: A System for automated nerve localization," *Regional Anesthesia*, 1992, 17(3): 151-162.

Shafik, Ahmen, "Cavernous Nerve Simulation through an Extrapelvic Subpubic Approach: Role in Pencil Erection," *Eur.Urol.*, 1994, 26: 98-102.

Toleikis et al., "The usefulness of electrical stimulation for assessing pedicle screw replacements," *Journal of Spinal Disorder*, 2000, 13(4): 283-289.

Welch et al., "Evaluation with evoked and spontaneous electromyography during lumbar instrumentation: a prospective study," *J. Neurosurg.* 87, Sep. 1997, pp. 397-402.

* cited by examiner

TISSUE DISCRIMINATION AND APPLICATIONS IN MEDICAL PROCEDURES

CROSS-REFERENCES TO RELATED APPLICATIONS

The present application is a continuation of U.S. patent application Ser. No. 11/439,780 entitled "Tissue Discrimination and Applications in Medical Procedures," filed May 23, 2006, which is a divisional of U.S. patent application Ser. No. 10/812,038, entitled "Tissue Discrimination and Applications in Medical Procedures," filed Mar. 29, 2004 and issued as U.S. Pat. No. 7,050,848 on May 23, 2006, which is a divisional of U.S. patent application Ser. No. 09/860,648, entitled "Tissue Discrimination and Applications in Medical Procedures", filed May 18, 2001 and issued as U.S. Pat. No. 6,760,616 on Jul. 6, 2004, which claims benefit under 35 U.S.C. §119(e) from U.S. Provisional Application Ser. No. 60/205,634 filed May 18, 2000 and U.S. Provisional Application Ser. No. 60/243,465 filed Oct. 25, 2000, the entire contents of which are each hereby expressly incorporated by reference into this disclosure as if set forth fully herein.

BACKGROUND OF THE INVENTION

I. Field of the Invention

The present invention is related to tissue surveillance systems.

II. Discussion of the Prior Art

Systems and methods exist for determining when a probe, needle, catheter or other devices make contact with a particular tissue, e.g. U.S. Pat. No. 5,836,990 to Li entitled "Method and Apparatus for Determining Electrode/Tissue Contact." The Li patent teaches a method for determining when a catheter makes contact with tissue covered with an ionic liquid. The system measures the electrical impedance at a distal end of the catheter and determines tissue contact has been made when the impedance increases. The system does not identify the type of tissue contacted and presumes the tissue is covered in an ionic liquid. Accordingly, a need exists for a system and method that identifies tissue and uses this information in medical procedures.

Systems and methods also exist for controlling the level of ablation of tissue. These systems monitor the impedance of tissue being ablated to determine if the ablation energy is optimal. The systems generally measure impedance to within approximately 20 ohms. These systems do not determine when sufficient therapy has been applied to the tissue or employ impedance measurement with low tolerance levels. Accordingly, a need exists for a system that may control any form of therapy by monitoring characteristics of an electrical signal applied to the tissue.

SUMMARY OF THE INVENTION

The present invention provides a system in which an electrical signal is applied to a tissue via electrodes disposed on a tissue probe. The electrical signal applied to the tissue preferably comprises a frequency variable current or voltage that is preferably applied to the tissue using a sliding frequency scale.

In accordance with the present invention, the response to the applied signal is measured as the signal passes through tissue disposed at, around, or adjacent to the probe. The inventors have found that different tissue types display different electrical transmission properties, including different capacitance and impedance properties. Accordingly, by measuring the electrical characteristics of the response signal, it is possible to determine the type of tissue through which the signal is passing. Preferably, this is accomplished by comparison to known exemplary signal characteristics for various tissue types. Furthermore, when the probe is known to be disposed within, around, or adjacent to a first tissue, the system and method may determine when the probe is advanced into a second tissue based on the changed electrical characteristics of the signal applied by the probe.

In accordance with the present invention, the electrical signal characteristics that are monitored may include the phase shift between the voltage and current passing through a selected tissue, and the impedance of the selected tissue. The inventors have experimentally determined that these properties vary from one tissue type to another. In a preferred aspect of the present invention, the electrical signal applied to the tissue may be a sliding frequency signal such that a frequency spectrum of phase shift and impedance of a tissue is determined. However, any electrical, magnetic, or optical signal with a measurable phase relationship and impedance to passage through the tissue can be used.

In a preferred method, a probe is advanced to a position in, at, or adjacent to a selected tissue and an electrical signal is applied to the tissue by an electrode on the probe. The response to this signal is then measured and compared against known electrical, magnetic, or optical transmission characteristics for the various tissue types. For example, the present invention provides a method and system for determining whether the conductive tip of a pedicle probe or pedicle screw is located in one of cortical bone, cancellous bone, and cortical bone near a boundary with soft tissue, whether the conductive tip of a cannula is located adjacent to one of nerve tissue and annulus tissue, and whether the conductive tip of a cathode is located adjacent to one of nerve tissue and prostate gland tissue.

Furthermore, the inventors have discovered that the signal transmission characteristics of various tissues vary as a function of the tissue's health. Accordingly, the present system can also be used to determine tissue health (for various tissue types) by comparing the signal responses of tissue in response to stimulation by the probe to responses for healthy tissue.

The inventors have also determined that different cell/tissue types exhibit different capacitive effects. In addition, these capacitive effects vary considerably between living and dead cells. Accordingly, in another aspect of the invention, the present system discriminates between living and dead tissues. This feature of the invention is particularly useful when the present system is used in conjunction with a tissue ablation system. For instance, the tissue ablation system may be prevented from providing unnecessary energy to ablate tissue and thereby protect surrounding tissue.

Moreover, the present system can be adapted to sense the presence of a particular type(s) of tissue as the probe is advanced through the patient's body. Such a feature is particularly advantageous when sensing for the presence of nerve tissue. Specifically, the probe can be advanced through the patient's body while the response to the electrical stimulation emitted by the probe is continuously monitored such that as nerve tissue is approached, the response signal will begin to exhibit characteristics indicative of nerve tissue.

Such nerve sensing features of the present invention can be used, for example, to sense for the presence of spinal nerves when advancing surgical equipment (which by way of example only may include cutting, drilling, screw insertion, implant, and tissue ablation systems) towards the patient's intervertebral space.

In an optional aspect of the present invention, a probe having an electrode positioned thereon is replaced with a probe that is itself electrified. For example, an electrified needle or an electrified trocar or cannula can be used as the probe. An advantage of having the entire probe emit the signal (rather than just an electrode disposed thereon) is that the probe itself can be made to smaller dimensions, particularly in the case of an electrified needle.

In optional aspects of the present invention, the probe is mono-polar. Specifically, only a first electrode is disposed on the probe. A second electrode is then positioned some distance away from the first electrode at another location on the body. Alternately, the probe may be bi-polar with both the first and second electrodes positioned on the probe itself. Additionally, the probe may include a plurality of bi-polar electrodes placed along the probe (such as around the tip and the length of the probe) to determine tissue types around the probe.

In a preferred aspect of the present invention, the measurement of the phase angle relationship between the voltage and current of the signal and impedance of the signal may be used to determine: (1) the type of tissue in which the probe is located; (2) the health of the tissue; (3) the relative location of the tip of the probe (e.g. in cases where the electrode is disposed in the tip of the probe); or (4) any combination of (1), (2) and (3). As such, by gathering data mapped by analyzing the response signal, measured characteristics can be used to correlate: (1) tissue identity, (2) tissue health, and (3) tissue location.

In addition, the present invention can be adapted to: (5) locate specific tissue within a body; (6) control application of therapy to tissue; (7) detect the state of health of a tissue; (8) navigate to tissue; and (9) any combination of the above-mentioned applications.

In one embodiment, the invention is a tissue system including a computer system having an analog- to-digital (A/D) converter and a digital-to-analog (D/A) converter interface (PCI board), that may be used to generate the control signal which is applied to the electrode or conductive tip of the probe. The computer generates the signal via the D/A converter. Then the A/D converter converts the signal received from the conductive tip into digital samples by sampling the signal at a predetermined rate where the digital samples may have a fixed or variable number of bits and have linear, logarithmic or other scaling. The computer system determines characteristics of the received signal from the digital samples, in particular the phase angle and impedance at the conductive tip or other location of the probe where the electrode(s) may be located. Based on the determined characteristics taken over time (which are then stored in a knowledge base or tabulated form), the present invention may determine tissue identity and tissue location. In a preferred aspect, the electrode disposed on the probe comprises a bipolar electrode conductive tip probe.

In an optional aspect of the present invention, the application of therapy to the tissue in which the probe is located may be precisely controlled, based on the characteristics of the tissue where the probe is located. For example, the application of heating or cooling therapy may be used to ablate or cool tissue. In one exemplary aspect, the same electrode(s) used for tissue discrimination (e.g. determining tissue type for tissue disposed adjacent to the electrode on the probe) may also be used for tissue ablation by heating.

In various aspects, the level of heating or cooling of the tissue may be modulated as a function of the measured characteristics of the tissue. In particular, the phase angle and impedance of the tissue change as the tissue is heated or cooled to a certain level. Accordingly, the application of therapy may be regulated by the present computer system. In particular, the computer system may communicate with a device applying therapy so as to automatically control the level of therapy.

Given that the present system can determine the type and location of various tissues within a patient, the present system may be used to determine the relative health of the tissue. In particular, the measured characteristics of the signal will vary for diseased or unhealthy tissue, as compared to normal healthy tissue. Thus, the present system may be used not only to determine the type and health of tissue, but also to control therapy for tissue based on the same. Furthermore, the probe may optionally be coupled with an automated navigation system that navigates within the patient based on the measured characteristics of the received signal. Such a navigation system may use the tissue identity and location data to navigate to a particular location within an organ. The computer system may then determine the health of the tissue at the location within the organ and control the application of therapy as appropriate.

As can be envisioned by one of ordinary skill in the art, many different combinations of the above features of the present invention may be used. Accordingly, the present invention is not limited by the scope of the appended claims.

In optional aspects of the invention, the characteristic electrical properties of the various tissue types are determined for different tissues at different RF frequencies. By way of example only, the signal may be emitted from the probe (into the surrounding tissue) at frequencies in the range of 400 kHz to 100 MHz. Determining the electrical properties of various tissues at various signal frequencies may be advantageous in that different cell (e.g. tissue) types may exhibit different harmonics. As such, tissues may be further characterized by measuring phase shift or impedance at various frequencies, or along a sliding frequency.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The tissue discrimination system and related methods disclosed herein boasts a variety of inventive features and components that warrant patent protection, both individually and in combination.

Figure 1:
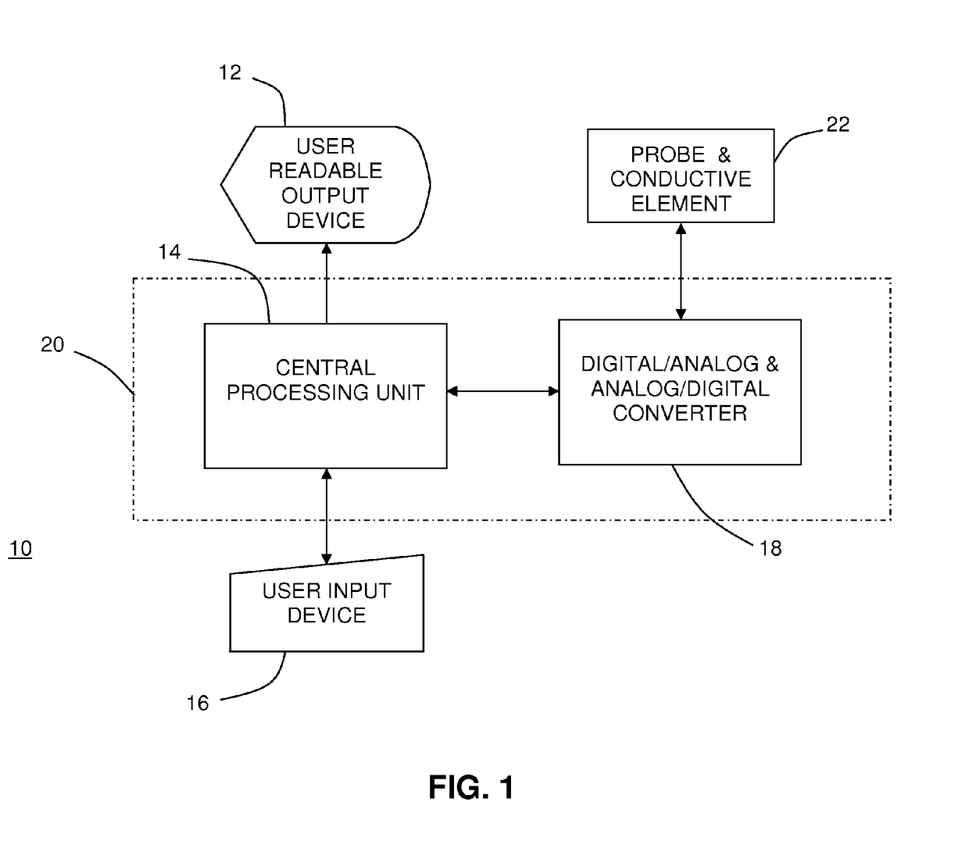
FIG. 1 is a block diagram of a tissue discrimination system in accordance with the present invention.

FIG. 1 is a diagram of a tissue identification system 10 in accordance with the present invention. The system 10 includes a user-readable output device 12, a user input device 16, a processor 20, and a probe 22. The processor 20 includes a central processing unit ("CPU") 14 and Digital-to-Analog Converter ("D/A") and Analog-to-Digital ("A/D") Converter 18. The CPU 14 may comprise any microprocessor having sufficient processing power to control the operation of the D/A & A/D 18 and output device 12. The D/A & A/D 18 may comprise any such device having a sufficient operating cycle to generate signals with the frequencies described herein and sufficient sampling rate to generate the digital samples described herein. The probe 22 may comprise any medical device that may be used to hold one or more electrodes thereon where the electrodes transmit and receive electrical signals. By way of example only, the probe 22 may consist of any such suitable medical instrument including but not limited to a cannula, needle, catheter, FR ablation device, or laser. The probe 22 may have a single electrode (mono-polar), two electrodes (bipolar), or a plurality of electrodes (multi-polar) configuration. Throughout the remainder of the discussion, a probe 22 with a conductive tip is discussed as one exemplary embodiment. It is understood that the electrodes could be placed anywhere along the circumference or width and length of the probe 22. A probe 22 having multiple electrodes ideally includes groups of bipolar electrodes so the system or method of the present invention may map the response of the electrode pairs.

The CPU 14 controls the operation of the D/A & A/D 18 and output device 12 based upon user selection received via the user input device 16. The user input device 16 may comprise any input device including but not limited to a keyboard, mouse, or touch-sensitive screen. The output device 12 may consist of any output device controllable by the CPU 14 including but not limited to a computer monitor, printer, or other computer controlled display device. The system 10 generates an electrical signal that is transmitted to tissue near or about the probe 22. When the probe 22 has an omni-directional conductive tip, the electrical signal may be propagated to a wide area of tissue about the conductive tip. The conductive tip may include an electrode pair (bipolar) so that the electrical signal is directed primarily to tissue directly in the path of the probe's 22 conductive tip (electrode pair). The system 10 provides an electrical signal at the electrode(s) on the probe 22 via the D/A 18. In particular, the CPU 14 generates a digital representation of a signal to be transmitted by the probe 22. The D/A 18 converts the digital signal to an analog signal that is transmitted through tissue by the probe 22.

The probe 22 also receives signals conducted by tissue surrounding the conductive tip of the probe 22. The A/D 18 converts the analog signal received by the electrode(s) of probe 22 into a digital signal that may be processed by the CPU 14.

In one embodiment, the system 10 applies a fixed frequency signal to the electrodes located on probe 22. In an exemplary embodiment, the applied signal may have a frequency ranging from 400 KHz to 100 MHz. The system 10 may further apply a signal having a range or sliding frequency. The system 10 applies this signal to the electrode(s) via the CPU 14 and D/A 18.

The repeatable pattern of the applied signal may be any pattern where the phase of the signal may be determined, e.g. any signal having a measurable phase relationship (voltage to current). In one embodiment, the applied signal may be sinusoidal in nature. In an alternative embodiment, the signal may be a square wave signal where the phase of the signal is measured at a leading or a trailing edge of each square wave. As previously stated, any signal with a measurable phase relationship (voltage to current) may be used.

The A/D 18 converts signals received at the electrode(s) of the probe 22 to a digital signal for processing by the CPU 14. The CPU 14 determines characteristics of the tissue surrounding the probe's 22 electrodes by comparing the signal applied to the electrode(s) and the signal received from the same. In one embodiment the phase angle between voltage and current of the applied signal (effective capacitance) and impedance of the tissue surrounding the conductive element (electrode(s)) of the probe 22 is determined. It has been found that the measurement of the phase angle relationship and impedance may be used to determine the identity or type of tissue in which the probe electrode(s) is located, the relative health of the tissue, the relative location of the electrodes to other surrounding tissue, and to control the application of therapy to the tissue surrounding the probe's 22 electrode(s). In one embodiment, the measured characteristics may be used to determine the identity or type of tissue in which the probe electrode(s) is located, the relative health of the tissue, the relative location of the tip to other surrounding tissue, and to control the application of therapy to the tissue surrounding the probe's 22 electrode(s).

For example, the probe 22 may be placed in the kidney of a patient. Then, system 10 may apply a signal to the probe's 22 electrode(s) having a varying or fixed frequency. Then the system 10 determines the phase angle and impedance of the signal applied to the probe 22 for each frequency of the signal. In one embodiment, the system 10 may use the combination of characteristics and frequency of the applied signal to determine 1) that the electrode(s) of the probe is located within kidney tissue (identification of tissue) and 2) the specific location within the kidney tissue where the probe is located, e.g., near the outer cordial or inner medulla of the kidney (specific identification of the tissue).

The system 10 may also determine whether the kidney tissue about the electrode(s) of the probe 22 is healthy, e.g., ischemic, or has tumors. By first knowing that the electrode(s) is in kidney tissue (a first tissue type), the system 10 can look for changes in the signal characteristics to determine that unhealthy tissue (a second tissue type) is present within the kidney. When the system 10 determines that the tissue about the probe's 22 electrode(s) is not healthy, the system 10 may apply therapy to the tissue. The therapy may include the application of heat energy (ablation) or removal of heat energy (cryogenic cooling) of the tissue. The system 10 may continue to monitor characteristics of the tissue about the electrode(s) to determine when sufficient therapy has been applied. Then, when sufficient therapy has been applied, the system 10 may stop the application of therapy. In one embodiment, sufficient therapy has been applied when the tissue dies. The system 10 may then monitor the phase angle and impedance of the applied signal to determine when cell or tissue necrosis has occurred. The system 10 may also consider the frequency of the applied signal relative to the phase angle and impedance.

The A/D converter 18 converts the signal received from the electrode(s) into digital samples by sampling the signal at a predetermined rate where the digital samples may have a fixed or variable number of bits and have linear, logarithmic or other forms of scaling. The system 10 determines characteristics of the received signal from the digital samples, in particular the phase angle and impedance at the electrode(s).

The system 10 may also include a knowledge base coupled to the CPU 14. The knowledge base may be stored characteristics about a large variety of known tissues. The base may also be correlated or indexed on the frequency of the applied signal. The knowledge base may be a database stored in a fixed electronic medium (not shown) coupled to the CPU 14. In this embodiment, the CPU 14 compares the determined characteristics to characteristics stored in the database to determine tissue identity, location, health, and control the application of therapy. It is noted that the invention may also know the current position of the electrode(s), e.g. in which tissue the electrode(s) is currently disposed. The knowledge base may further include information that correlates to known current position of electrode(s) (within a first tissue) with measured characteristics so the system 10 may determine a second tissue type. Accordingly, the system 10 or method of the invention may determine the tissue type of a second tissue based on knowledge of the position of the electrode(s) in a previous first tissue and measured characteristics of the signal applied to the electrode(s).

It is noted that in another embodiment, the present invention may be used with a device that automatically navigates through tissue. By way of example only, the present invention may be coupled to an automated catheter system. The system 10 would provide tissue identity and location to the navigation system so the navigation system may navigate to a desired location. Once at the desired location, the system 10 may determine the health of the tissue. Then, the system 10 may control the application of therapy to the tissue based on the determined health of the tissue.

Figure 2:
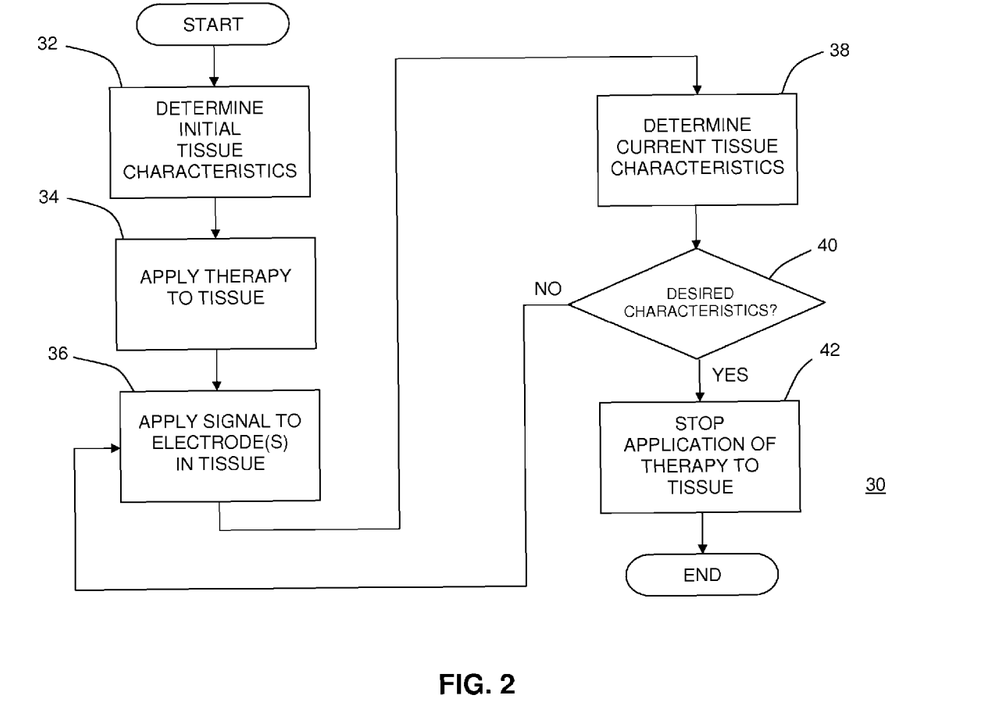
FIG. 2 illustrates a method of controlling the application therapy to tissue according to the present invention.

For example, a navigation system used in conjunction with system 10 may direct the probe 22 to a specific location within kidney tissue. Based on the known characteristics of the tissue, the health of the tissue may be determined and the application of therapy may be applied when needed. A method 30 of applying therapy is shown in FIG. 2. In step 32, the method 30 first determines the initial characteristics of the tissue. Then therapy is applied to the tissue (step 34). Therapy for the kidney tissue may include the application of heat or cooling therapy to ablate or cool the tissue. The level of heating or cooling of the tissue may be modulated as a function of the measured characteristics of the tissue. In particular, the phase angle and impedance of the tissue will change as the tissue is heated or cooled to a certain level. The method 30 applies a signal to electrode(s) in the tissue receiving therapy (step 36). The method 30 then determines the current tissue characteristics based on the applied signal (step 38). When the desired tissue characteristics are present (sufficient therapy applied) (step 40), the method 30 stops the application of therapy to the tissue (step 42). If, on the other hand, the desired tissue characteristics are not achieved, the method 30 returns to the step of applying a signal to the electrode(s) in tissue (step 36) and again progresses through the remaining steps. Accordingly, the application of therapy may be regulated by the system 10. In one embodiment, the system 10 communicates with a device applying therapy and automatically controls the level of therapy.

Figure 3:
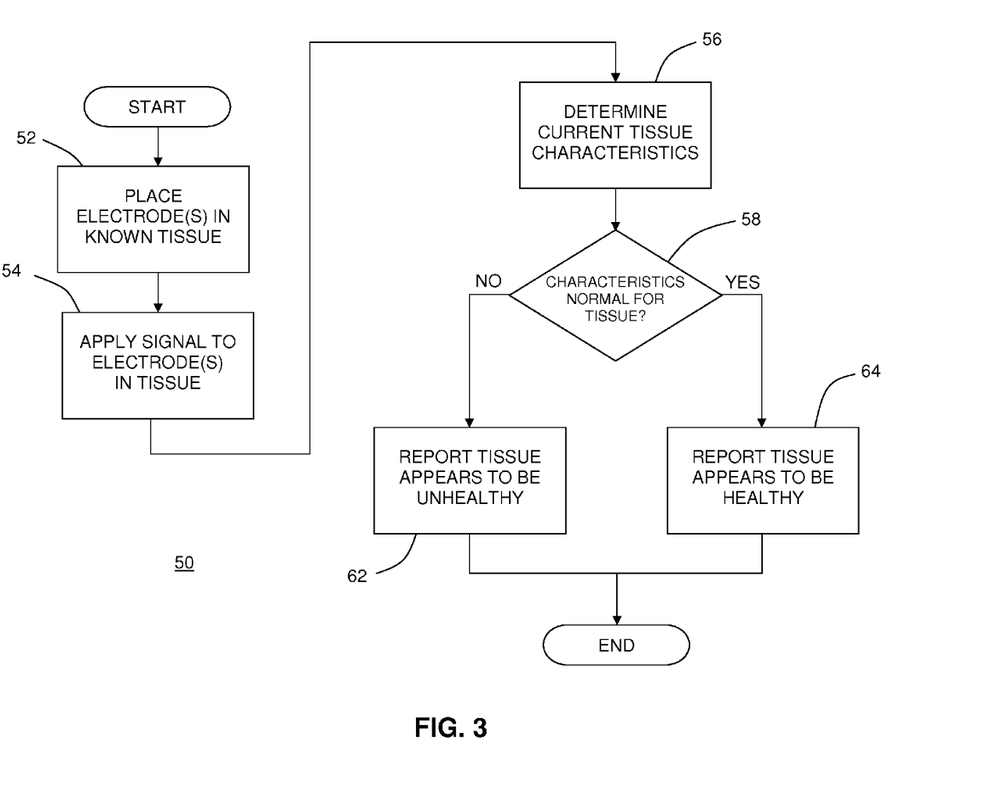
FIG. 3 illustrates a method of determining tissue health according to the present invention.

As noted, the system 10 may be used to determine the relative health of a tissue. The measured characteristics of the signal will vary for diseased or unhealthy tissue. For example, it has been found that cancerous cells have measurably different impedance from that of healthy tissue. FIG. 3 illustrates a method 50 of determining tissue health according to the present invention. The method 50 places the electrode(s) in known tissue (step 52). The tissue may be known by first determining the location of the electrode(s) using techniques described above. Then the method 50 applies a signal to the electrode(s) in the tissue of interest (step 54). The signal may be a signal of varying frequency, e.g. a sliding frequency signal in one embodiment. The method 50 then determines the tissue characteristics based on the applied signal (step 56). The determined characteristics are compared to normal or expected characteristics for health or normal known tissue (step 58). When the determined characteristics are different from the expected characteristics for the known tissue (when healthy) (by some tolerance amount), the method 50 indicates that the tissue at the electrode(s) is unhealthy (step 62). The method 50 may also indicate what type of disease the tissue may have based on known characteristics of diseased tissue e.g. tissue appears to be cancerous or ischemic. Otherwise, the system may report that the tissue near the electrode(s) appears to be healthy (step 64).

In another embodiment, the probe 22 may be a pedicle screw or pedicle probe. During the insertion of a pedicle screw, it is critical that the pedicle wall is not violated. Surgeons use image intensifiers and other equipment to prevent such a violation. The tissue discrimination system 10 of the present invention may be used to monitor the position of the pedicle probe or pedicle screw. In particular, the system 10 monitors the impedance and capacitance or phase shift at the tip of the pedicle probe or screw to determine whether the tip is in cortical bone, cancellous bone, or cortical bone near a boundary with soft tissue.

In this embodiment, the outer surface of the pedicle screw may be non-conductive except for the surface of the head and tip of the pedicle screw. Likewise, the outer surface of the pedicle probe is non-conductive except for the distal and proximal ends of the probe. A conductive lead is then applied to the head of the pedicle screw or proximal end of the pedicle probe to conduct a signal to the tip of the screw or probe. In one embodiment, the signal may have a fixed or varying frequency. The system 10 then determines the phase angle and impedance of the signal applied to the tip for each frequency of the signal. To accomplish this, the system 10 may use the combination of characteristics and frequency of the applied signal to determine whether the tip is located in cortical bone, cancellous bone, or cortical bone near the boundary with soft tissue. Depending on this determination, the surgeon may continue the insertion of the pedicle probe or screw.

In another embodiment, the probe 22 may be a cannula to be inserted adjacent to an annulus of a patient's spinal disc prior to performing an annulotomy. During the insertion of the cannula towards the annulus, it is critical that the cannula not rest against a nerve along side the annulus wall. Surgeons use electromyography (EMG) equipment and other equipment to prevent such a situation. The tissue discrimination system 10 of the present invention may be used to monitor the position of the cannula as it is advanced to the annulus wall. In particular, the system 10 monitors the impedance and capacitance or phase shift at the tip of the cannula to determine whether the distal tip is adjacent to nerve tissue or annulus tissue.

In this embodiment, the outer surface of the cannula is non-conductive except for the distal and proximal ends of the cannula. A conductive lead is then applied to the proximal end of the cannula to conduct a signal to the tip of the cannula, the signal having a fixed or varying frequency. The system 10 then determines the phase angle and impedance of the signal applied to the tip for each frequency of the signal. To accomplish this, the system 10 may use the combination of characteristics and frequency of the applied signal to determine whether the tip is located adjacent to nerve tissue or annulus tissue. Depending on this determination, the surgeon may continue the insertion of the cannula.

In another embodiment, the probe 22 may be an ablation cathode to be inserted into a patient's prostate gland prior to performing prostate gland ablation. During the insertion of the cathode into the prostate gland, it is critical that the cathode is not near or adjacent to nerve tissue along side or within the prostate gland. Surgeons use image intensifier equipment and other equipment to prevent such a situation. The tissue discrimination system 10 of the present invention may be used to monitor the position of the cathode as it is advanced into the prostate gland. In particular, the system 10 monitors the impedance and capacitance or phase shift at the tip of the cathode to determine whether the distal tip is adjacent to nerve tissue or prostate gland tissue.

In this embodiment, a signal is applied to the ablation cathode tip, the signal having a fixed or varying frequency. The system 10 then determines the phase angle and impedance of the signal applied to the tip for each frequency of the signal. To accomplish this, the system 10 may use the combination of characteristics and frequency of the applied signal to determine whether the tip is located adjacent to nerve tissue or prostate gland tissue. Depending on this determination, the surgeon may continue the insertion of the cathode.

While this invention has been described in terms of the best mode for achieving this invention's objections, it will be appreciated by those skilled in the art that variations may be accomplished in view of these teachings without deviating from the spirit or scope of the present invention. For example, the present invention may be implemented using any combination of computer programming software, firmware, or hardware. As a preparatory step to practicing the invention or constructing an apparatus according to the invention, the computer programming code (whether software or firmware) according to the present invention will typically be stored in one or more machine readable storage mediums such as fixed (hard) drives, diskettes, optical disks, magnetic tape, semiconductor memories such as ROMs, PROMs, etc., thereby making an article of manufacture in accordance with the invention. The article of manufacture containing the computer programming code is used by either executing the code directly from the storage device, by copying the code from the storage device into another storage device such as a hard disk, RAM, etc. or by transmitting the code on a network for remote execution.

As can be envisioned by one of skill in the art, many different combinations of the above may be used and accordingly the present invention is not limited by the scope of the appended claims.

What is claimed is:

1. A system for preventing violation of a cortical wall of a pedicle during spine surgery, said pedicle including a cancellous core within said cortical wall, said system comprising:
   (a) a screw configured for advancement and purchase into said pedicle and having a non-conductive shaft and a conductive tip; and
   (b) a processor in electrical communication with the screw, the processor configured to direct application of an electrical signal to the conductive tip and determine at least one of the capacitance and impedance characteristics of the tissue adjacent to said conductive tip to determine whether said conductive tip lies within or adjacent cortical bone, cancellous bone, and cortical bone near the boundary with soft tissue.

2. The system of claim 1, wherein said conductive tip comprises a bi-polar electrode.

3. The system of claim 1, wherein the determined characteristics of the tissue further include a phase angle relationship between a voltage and current of the applied electrical signal.

4. The system of claim 1, wherein the applied electrical signal has a range of predetermined frequencies.

5. The system of claim 4, wherein the range of predetermined frequencies is from 400 KHz to 100 MHz.

6. The system of claim 1, wherein the applied signal has a fixed frequency.

7. The system of claim 1, wherein the applied electrical signal has a sliding frequency.

8. The system of claim 1, wherein the applied signal is a sinusoidal signal.

9. The system of claim 1, wherein the applied signal is a square wave signal.

10. The system of claim 1, further comprising an output element for communicating feedback regarding said measured characteristics.

11. The system of claim 1, further comprising an input device for receiving instructions from a user.

12. The system of claim 1, wherein said screw further comprises a conductive head.

13. A method for preventing violation of a cortical wall of a pedicle during spine surgery, said pedicle including a cancellous core within said cortical wall, comprising the steps of:
   (a) advancing a pedicle screw into at least one of said cancellous core and said cortical wall of said pedicle during spine surgery, said pedicle screw having a conductive tip for measuring impedance;
   (b) delivering an electrical signal to said conductive tip during step (a);
   (c) measuring the impedance of at least one of said cancellous core and said cortical wall during step (a); and
   (d) stopping the advancement of said pedicle screw based on a change in said measured impedance from step (c) to prevent a violation of said cortical wall by the continued advancement of said pedicle screw.

14. The method of claim 13, further comprising the step of communicating feedback to said user.

15. The method of claim 13, wherein the delivery of said electrical signal of step (b) and the measuring of impedance of step (c) are performed by a processor in electrical communication with said pedicle screw.

16. The method of claim 14, wherein the communication of feedback to said user is performed by an output element.

17. The method of claim 13, wherein said conductive tip comprises a bi-polar electrode.

18. The method of claim 13, wherein step (b) includes delivering said electrical signal with at least one of a fixed frequency and a sliding frequency.

19. A method for preventing violation of a cortical wall of a pedicle during spine surgery, said pedicle including a cancellous core within said cortical wall, comprising the steps of:
   (a) advancing a pedicle screw through said cancellous core of said pedicle during spine surgery, said pedicle screw having a conductive tip for measuring impedance;
   (b) measuring the impedance adjacent the conductive tip during step (a);
   (c) viewing feedback from an output element; and
   (d) stopping the advancement of said pedicle screw if said measured impedance indicates said conductive tip is not within said cancellous core to prevent a violation of said cortical wall by the continued advancement of said pedicle screw.

20. The method of claim 19, wherein the measuring of impedance of step (b) is performed by a processor in electrical communication with said pedicle screw.

21. The method of claim 19, wherein said output element is a computer display.

22. The method of claim 19, wherein said conductive tip comprises a bi-polar electrode.

23. The method of claim 19, wherein step (b) includes delivering an electrical signal to said conductive tip, said electrical signal having at least one of a fixed frequency and a sliding frequency.

* * * * *